United States Patent
Kaneko et al.

(10) Patent No.: US 10,478,641 B2
(45) Date of Patent: Nov. 19, 2019

(54) RADIOTHERAPY DEVICE CONTROL APPARATUS AND CONTROL METHOD

(71) Applicant: Hitachi, Ltd., Tokyo (JP)

(72) Inventors: Shuji Kaneko, Tokyo (JP); Kunio Takahashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 235 days.

(21) Appl. No.: 15/547,394

(22) PCT Filed: Jan. 29, 2015

(86) PCT No.: PCT/JP2015/052569
§ 371 (c)(1),
(2) Date: Jul. 28, 2017

(87) PCT Pub. No.: WO2016/121067
PCT Pub. Date: Aug. 4, 2016

(65) Prior Publication Data
US 2018/0008842 A1 Jan. 11, 2018

(51) Int. Cl.
*A61N 5/10* (2006.01)

(52) U.S. Cl.
CPC ......... *A61N 5/1049* (2013.01); *A61N 5/1045* (2013.01); *A61N 5/1081* (2013.01);
(Continued)

(58) Field of Classification Search
CPC ...... A61N 5/10; A61N 5/1045; A61N 5/1049; A61N 5/103; A61N 2005/1051; A61N 2005/1061; A61N 5/1081
See application file for complete search history.

(56) References Cited

U.S. PATENT DOCUMENTS

| | | | |
|---|---|---|---|
| 5,818,902 A | 10/1998 | Yu | |
| 6,937,696 B1 * | 8/2005 | Mostafavi | A61B 5/113 378/65 |

(Continued)

FOREIGN PATENT DOCUMENTS

| | | | |
|---|---|---|---|
| JP | H10-328318 A | 12/1998 | |
| JP | 2006-288875 A | 10/2006 | |

(Continued)

OTHER PUBLICATIONS

Extended European Search Report for application No. 15879964.3, dated Oct. 8, 2018, 7 pages.

(Continued)

*Primary Examiner* — Christine H Matthews
*Assistant Examiner* — Joshua Daryl D Lannu

(57) ABSTRACT

A radiotherapy device control apparatus instructs a radiotherapy device to execute instruction information based on a treatment regimen determined in advance, controls the operations of an irradiation-related instrument provided in the radiotherapy device on the basis of irradiation conditions included in the instruction information, determines whether irradiation is permitted on the basis of results detected by an irradiation target detection unit that detects movement of a target to be irradiated, controls execution and interruption of therapeutic irradiation on the basis of the determined result, stores the history of interruption of irradiation according to the determination by the irradiation permission determination unit, and causes the instrument to run the operations based on the instruction information to completion, regardless of whether irradiation has been interrupted during execution of the instruction information.

11 Claims, 6 Drawing Sheets

(52) U.S. Cl.
CPC ................. *A61N 2005/1051* (2013.01); *A61N 2005/1061* (2013.01)

(56) References Cited

U.S. PATENT DOCUMENTS

| | | | | |
|---|---|---|---|---|
| 8,437,449 | B2 * | 5/2013 | Riley | ..................... A61N 5/103 |
| | | | | 378/65 |
| 8,637,837 | B2 * | 1/2014 | Natori | ................... A61N 5/1043 |
| | | | | 250/492.1 |
| 2006/0231775 | A1 | 10/2006 | Harada | |
| 2009/0041200 | A1 * | 2/2009 | Lu | ........................ A61N 5/1042 |
| | | | | 378/152 |

FOREIGN PATENT DOCUMENTS

| | | |
|---|---|---|
| JP | 2008-237687 A | 10/2008 |
| JP | 2009-045229 A | 3/2009 |
| JP | 2013-009967 A | 1/2013 |

OTHER PUBLICATIONS

International Search Report for PCT Patent Application No. PCT/JP2015/052569, dated Mar. 10, 2015, 2 pages.

* cited by examiner

RADIOTHERAPY DEVICE CONTROL APPARATUS AND CONTROL METHOD

CROSS-REFERENCE TO RELATED APPLICATION

This application is a national phase claiming the benefit of and priority to International Patent Application No. PCT/JP2015/052569, entitled "RADIOTHERAPY DEVICE CONTROL APPARATUS AND CONTROL METHOD" filed Jan. 29, 2015, which is hereby incorporated by reference in its entirety.

TECHNICAL FIELD

The present disclosure relates to a radiotherapy device control apparatus, and a control method.

BACKGROUND

Radiotherapy devices include, for example, devices that enable dynamic conformal arc to irradiate therapeutic radiation intensively on an affected part by irradiating the therapeutic radiation while adjusting an irradiation field corresponding to a shape of the affected part using a multi leaf collimator (MLC) from a plurality of directions (Patent Literature 1). Patent Literature 1 further describes a volumetric modulated arc therapy (VMAT) in which the radiation is irradiated while a gantry is rotated.

CITATION LIST

Patent Literature

Patent Literature 1: U.S. Pat. No. 5,818,902

SUMMARY

Technical Problem

When interruption of the irradiation becomes necessary and the irradiation is interrupted, the irradiation of the therapeutic radiation will be re-started by a re-start operation by an operator. In this process, in therapies such as Dynamic IMRT (Intensity Modulated Radiation Therapy), Dynamic Conformal Arc, Dynamic WaveAarc, VMAT, or the like, generally, the position is returned to the interrupted position or a position slightly before the interruption, and the irradiation as planned is executed by again starting the irradiation of the therapeutic radiation from the position passed the interrupted position by executing a sequence of mechanical operations.

In addition, radiotherapy devices include a device having a mechanism to recognize, for a tumor which moves with respiration such as lung cancer, a position of the tumor in real time, and irradiate the therapeutic radiation while tracking the position of the tumor. In such devices, a control is applied such that, when the control of the irradiation direction of the radiation cannot follow the motion due to rapid disturbance in the respiration or the like, the irradiation is automatically interrupted, to secure safety.

However, there may be cases where, due to a respiration state of the patient on that day, deviation of the irradiation position of the therapeutic radiation exceeding an allowable range occurs frequently, and irradiation is interrupted every time the deviation occurs. In this case, the sequence of mechanical operations must be repeated every time the irradiation is interrupted, which may cause problems such as an increase in the therapy time, and stress exerted on the patient and/or the therapist.

An advantage of the present disclosure lies in provision of a radiotherapy device control apparatus and a control method which can resolve the above-described problem.

Solution to Problem

According to a first aspect of the present disclosure, there is provided a radiotherapy device control apparatus comprising: a therapy plan execution unit that instructs execution of instruction information based on a therapy plan which is defined in advance; an irradiation operation controller that controls an operation of a device related to irradiation provided on a radiotherapy device, based on an irradiation condition included in the instruction information; an irradiation possibility judging unit that judges whether or not irradiation is possible based on a detection result of an irradiation target detector that detects a motion of an irradiation target; an irradiation controller that controls execution and interruption of irradiation of a therapeutic radiation based on a result of the judgment; and an irradiation recorder that records an interruption history of irradiation by the judgment of the irradiation possibility judging unit, wherein the irradiation operation controller executes the operation of the device based on the instruction information to the last operation regardless of presence or absence of an interruption of the irradiation during execution of the instruction information.

According to a second aspect of the present disclosure, in the radiotherapy device control apparatus, the therapy plan execution unit repeatedly instructs, after the instruction information is executed and when an interruption history of irradiation is recorded by the irradiation recorder, execution of the instruction information until there is no record of the interruption history of the irradiation, the irradiation operation controller controls the operation of the device based on the instruction, and the irradiation controller executes irradiation only for an irradiation interruption period recorded in the interruption history.

According to a third aspect of the present disclosure, in the radiotherapy device control apparatus, the therapy plan execution unit produces, after the instruction information is executed and when one or a plurality of interruption histories of irradiation are recorded by the irradiation recorder, new instruction information targeted to a continuous range including all of the irradiation interruption periods recorded in the interruption history, and instructs the irradiation operation controller to execute the new instruction information.

According to a fourth aspect of the present disclosure, in the radiotherapy device control apparatus, the irradiation possibility judging unit calculates a difference between a position of an irradiation target calculated based on a correlation model of a respiration signal and an irradiation position, which is defined in advance and a respiration signal which is generated in synchronization with respiration of a body to be irradiated detected by the irradiation target detector, and a position of the irradiation target acquired from an image of the body to be irradiated detected by the irradiation target detector, judges that irradiation is possible if the difference is within a predetermined range, and judges that irradiation is not possible if the difference is outside of the predetermined range.

According to a fifth aspect of the present disclosure, the device related to irradiation is a gantry which rotates an irradiation unit around an axis in a horizontal direction, and the irradiation operation controller controls a rotational angle of the gantry.

According to a sixth aspect of the present disclosure, the device related to irradiation is a ring which rotates an irradiation unit around an axis in a vertical direction, and the irradiation operation controller controls a rotational angle of the ring.

According to a seventh aspect of the present disclosure, the device related to irradiation is a ring which rotates an irradiation unit around an axis in a vertical direction and a gantry which rotates an irradiation unit around an axis in a horizontal direction, and the irradiation operation controller controls a rotational angle of the ring and a rotational angle of the gantry.

According to an eighth aspect of the present disclosure, in the radiotherapy device control apparatus, the irradiation operation controller determines, after the instruction information is executed and when an interruption history of irradiation is recorded by the irradiation recorder, a rotational direction of the device related to irradiation based on a position of the irradiation interruption period recorded in the interruption history.

According to a ninth aspect of the present disclosure, the device related to irradiation is a multi leaf collimator, and the irradiation operation controller controls a position of each leaf of the multi leaf collimator.

According to a tenth aspect of the present disclosure, the device related to irradiation is a swing mechanism which supports an irradiation unit, and the irradiation operation controller controls a rotational angle of at least one of a pan axis and a tilt axis of the swing mechanism.

According to an eleventh aspect of the present disclosure, there is provided a control method of a radiotherapy device, comprising: instructing execution of instruction information based on a therapy plan which is defined in advance; controlling an operation of a device related to irradiation provided on the radiotherapy device, based on an irradiation condition included in the instruction information; judging whether or not irradiation is possible based on a detection result of an irradiation target detector that detects a motion of an irradiation target; controlling execution and interruption of irradiation of a therapeutic radiation based on a result of the judgment; recording an interruption history of irradiation by the judgment; and executing the operation of the device based on the instruction information to the last operation regardless of presence or absence of an interruption of irradiation during execution of the instruction information.

Advantageous Effects of Invention

According to the above-described aspects of the present disclosure, therapy time by the radiotherapy device can be shortened.

DESCRIPTION OF EMBODIMENTS

<First Embodiment>

A radiotherapy system according to a first embodiment of the present disclosure will now be described with reference to FIGS. 1-7.

Figure 1:
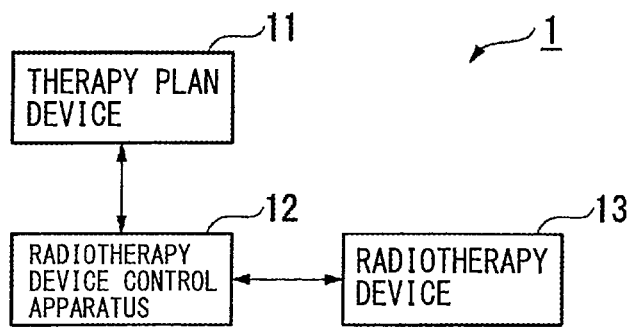
FIG. 1 is a schematic block diagram showing a functional structure of a radiotherapy system according to a first embodiment of the present disclosure.

FIG. 1 is a schematic block diagram showing a functional structure of a radiotherapy system according to the first embodiment of the present disclosure. In FIG. 1, the radiotherapy system 1 comprises a therapy plan device 11, a radiotherapy device control apparatus 12, and a radiotherapy device 13.

The radiotherapy system 1 is a system for radiotherapy. Specifically, the radiotherapy system 1 irradiates radiation (therapeutic radiation). The therapeutic radiation irradiated by the radiotherapy system 1 may be an electromagnetic wave such as an X-ray, or a particle beam such as a baryon beam or a proton beam.

In particular, the radiotherapy system 1 executes radiation irradiation by tracking irradiation. The tracking irradiation refers to a method of controlling the radiotherapy device 13 such that position information of an irradiation target which moves by respiration or the like is acquired in real time, and the radiation is continuously irradiated onto the irradiation target. The irradiation target is a portion of the target of therapeutic radiation irradiation within a body of the patient such as a tumor.

The therapy plan device 11 produces a therapy plan for the radiotherapy system 1 to irradiate the therapeutic radiation. The therapy plan is information indicating the contents of control executed by the radiotherapy device control apparatus 12 on the radiotherapy device 13. Specifically, the therapy plan produced by the radiotherapy system 1 indicates a plan as to how the radiotherapy device 13 is to be operated to irradiate the therapeutic radiation.

The radiotherapy device control apparatus 12 controls the radiotherapy device 13 according to the therapy plan produced by the therapy plan device 11, and causes the radiotherapy device 13 to irradiate therapeutic radiation by tracking irradiation. The radiotherapy device control apparatus 12 is formed, for example, to include a computer. In particular, the radiotherapy device control apparatus 12 produces a correlation model indicating a relationship between a respiration signal and a position of the irradiation target of the radiation, detects a position of the irradiation target using the correlation model, and executes control of the radiotherapy device.

The radiotherapy device 13 executes the irradiation of the therapeutic radiation according to the control of the radiotherapy device control apparatus 12.

Figure 2:
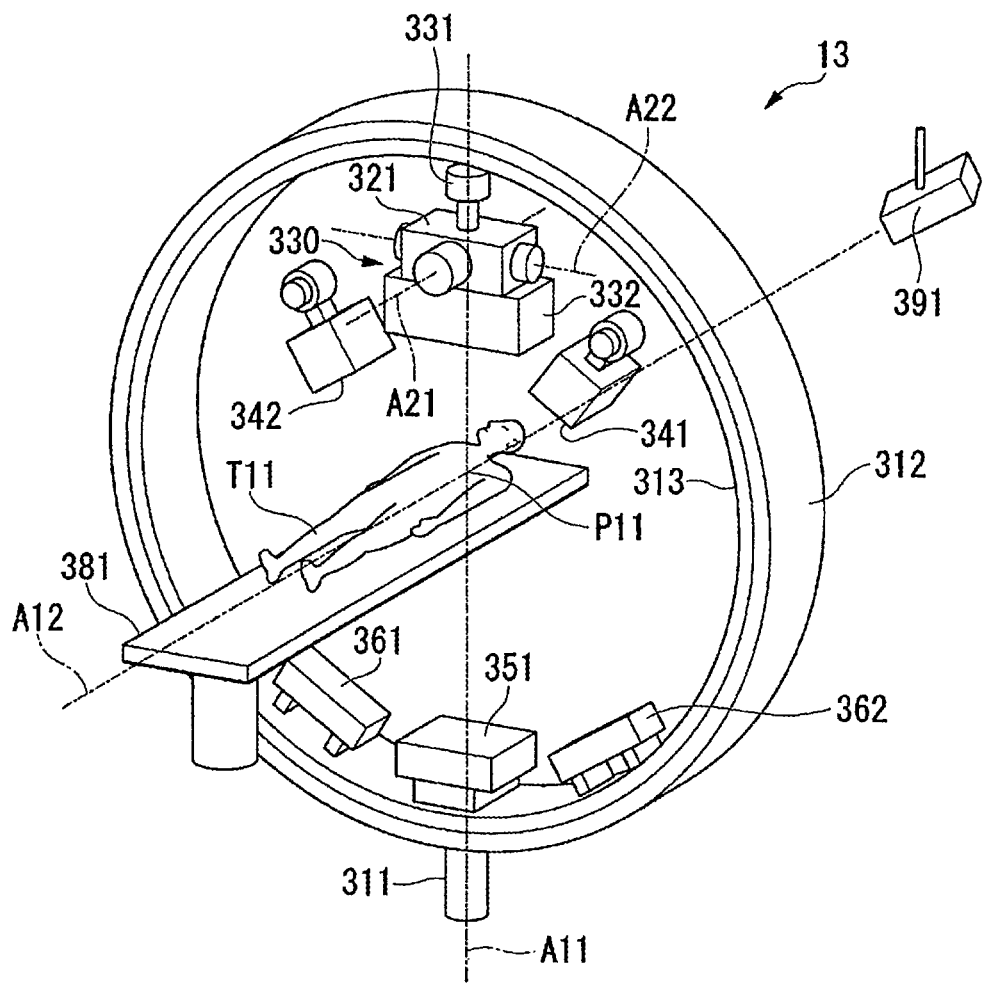
FIG. 2 is a schematic structural diagram showing a device structure of a radiotherapy device according to the first embodiment of the present disclosure.

FIG. 2 is a schematic structural diagram showing a device structure of the radiotherapy device 13. In FIG. 2, the radiotherapy device 13 comprises a turn drive device 311, an O-ring 312, a travel gantry 313, a swing mechanism (gimbal mechanism) 321, an irradiation unit 330, sensor arrays 351, 361, and 362, and a couch 381. The irradiation unit 330 comprises a radiation irradiation device 331, a multi leaf collimator 332, imaging radiation sources 341 and 342, and an infrared (IR) camera 391.

The turn drive device 311 supports the O-ring 312 on a base in a rotatable manner about a rotational axis A11, and rotates the O-ring 312 according to control of the radiotherapy device control apparatus 12. The rotational axis A11 is an axis in a vertical direction.

The O-ring 312 is formed in a ring shape centered at a rotational axis A12, and supports the travel gantry 313 in a rotatable manner around the rotational axis A12. The rotational axis A12 is an axis in a longitudinal direction of the couch 381. In addition, the rotational axis A12 is an axis in the horizontal direction (that is, an axis at a right angle to the vertical direction), and is orthogonal to the rotational axis A11 at an isocenter P11. The rotational axis A12 is fixed with respect to the O-ring 312. That is, the rotational axis A12 rotates about the rotational axis A11, with the rotation of the O-ring 312.

The travel gantry 313 is formed in a ring shape centered at the rotational axis A12, and is placed so as to be in a concentric circle with the O-ring 312 at an inner side of the O-ring 312. The radiotherapy device 13 further comprises a travel drive device (not shown), and the travel gantry 313 rotates about the rotational axis A12 by a motive force from the travel drive device.

A self-rotation of the travel gantry 313 causes integral rotation of components provided on the travel gantry 313 such as the imaging radiation source 341 and the sensor array 361, or the imaging radiation source 342 and the sensor array 362.

The swing mechanism 321 is fixed on the travel gantry 313 at an inner side of the ring, and supports the irradiation unit 330 on the travel gantry 313. The swing mechanism 321 supports the irradiation unit 330 in a manner to allow change of orientation, and changes the orientation of the irradiation unit 330 according to the control of the radiotherapy device control apparatus 12. Specifically, the swing mechanism 321 rotates the irradiation unit 330 about a pan axis A21 parallel to the rotational axis A12. In addition, the swing mechanism 321 rotates the irradiation unit 330 about a tilt axis A22 which is orthogonal to the pan axis A21.

The irradiation unit 330 is supported and placed on the swing mechanism 321 at an inner side of the travel gantry 313, and irradiates the therapeutic radiation and an imaging radiation.

The radiation irradiation device 331 irradiates the therapeutic radiation toward an affected part of a patient T11 according to the control of the radiotherapy device control apparatus 12. The radiation irradiation device 331 irradiates therapeutic radiation B11. Because the radiation irradiation device 331 is supported on the travel gantry 313 via the swing mechanism 321, when the radiation irradiation device 331 is directed toward the isocenter P11 by adjustment of the swing mechanism 321, even if the O-ring 312 is rotated by the turn drive device 311 or the travel gantry 313 is rotated by the travel drive device, the therapeutic radiation B11 would always substantially passes through the isocenter P11. Therefore, the radiation irradiation device 331 can irradiate the therapeutic radiation B11 toward the isocenter P11 from various directions by rotating about the rotational axis A11 and the rotational axis A12.

The multi leaf collimator 332 opens and closes a leaf according to the control of the radiotherapy device control apparatus 12, to block a part of or all of the therapeutic radiation. With this process, the multi leaf collimator 332 adjusts an irradiation field when the therapeutic radiation is irradiated onto the patient T11.

The imaging radiation source 341 irradiates the imaging radiation (X-ray) toward the sensor array 361 according to the control of the radiotherapy device control apparatus 12. The imaging radiation source 342 irradiates the imaging radiation toward the sensor array 362 according to the control of the radiotherapy device control apparatus 12. The imaging radiation sources 341 and 342 are fixed on the irradiation unit 330 (for example, a housing of the multi leaf collimator 332) in an orientation where the irradiated radiations thereof are orthogonal to each other.

The sensor array 351 is placed at a position where the therapeutic radiation from the radiation irradiation device 331 hits, in an orientation facing the radiation irradiation device 331, and is fixed on the travel gantry 313 at an inner side of the ring. The sensor array 351 receives the therapeutic radiation which transmits through the patient T11 or the like, for checking the irradiation position and for therapeutic recording. The reception here means reception of the radiation.

The sensor array 361 is placed at a position where the imaging radiation from the imaging radiation source 341 hits, in an orientation facing the imaging radiation source 341, and fixed on the travel gantry 313 at an inner side of the ring. The sensor array 361 receives the imaging radiation which is irradiated from the imaging radiation source 341 and which transmits through the patient T11 or the like, for identifying a position of an affected part.

By the sensor array 361 receiving the imaging radiation from the imaging radiation source 341, a radiation image is acquired.

The sensor array 362 is placed at a position where the imaging radiation from the imaging radiation source 342 hits, in an orientation facing the imaging radiation source 342, and is fixed on the travel gantry 313 at an inner side of the ring. The sensor array 362 receives the imaging radiation which is irradiated from the imaging radiation source 342 and which transmits through the patient T11 or the like, for identifying a position of an affected part.

By the sensor array 362 receiving the imaging radiation from the imaging radiation source 342, a radiation image is acquired. In particular, by the combination of the imaging radiation source 342 and the sensor array 362, a radiation image is acquired from a direction different from that of the combination of the imaging radiation source 341 and the sensor array 361.

By the combination of the imaging radiation source 341 and the sensor array 361 or the combination of the imaging radiation source 342 and the sensor array 362, information indicating the position of the irradiation target is acquired when a correlation model for tracking irradiation to be described later is to be produced. Specifically, with the combination of the imaging radiation source 341 and the sensor array 361 and the combination of the imaging radiation source 342 and the sensor array 362, two-dimensional see-through images of the irradiation target imaged from different angles are obtained. Based on the two-dimensional see-through images from two directions, three-dimensional position information of the irradiation target is acquired.

The structure of an irradiation target position information acquisition device is not limited to the combination of the imaging radiation source 341 and the sensor array 361, and the combination of the imaging radiation source 342 and the sensor array 362, and there may be employed various structures which can acquire the position information of the irradiation target. For example, as the irradiation target position information acquisition device, a position measurement device which outputs position information may be embedded near the irradiation target.

The couch 381 is used for the patient T11 to lie on the side, and supports the patient T11. The couch 381 is placed in a manner such that the longitudinal direction faces the direction of the rotational axis A12. The couch 381 can be moved in various directions while keeping the longitudinal direction directed toward the rotational axis A12.

The infrared (IR) camera 391 receives infrared ray, and images an infrared image. In particular, the infrared camera 391 is placed facing the patient T11 lying on the sides on the couch 381. The infrared camera 391 images an infrared marker provided on a body surface near the affected part of the patient T11, and acquires position information of the infrared marker in real time. In particular, the infrared camera 391 acquires in correspondence to time information the position information of the infrared marker at that time.

Figure 3:
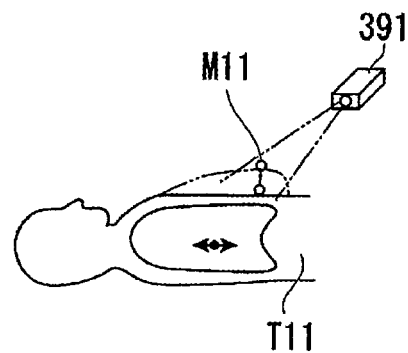
FIG. 3 is an explanatory diagram showing an example placement of an infrared marker imaged by an infrared camera in the first embodiment of the present disclosure.

FIG. 3 is an explanatory diagram showing an example placement of the infrared marker imaged by the infrared camera 391. In the example configuration of FIG. 3, an infrared marker M11 is provided on a surface of an abdomen of the patient T11. The infrared marker M11 periodically moves in synchronization with the respiration of the patient T11, and the position information acquired by the infrared camera 391 imaging the infrared marker M11 corresponds to an example of a respiration signal which is a signal generated in synchronization with the respiration.

During irradiation of the therapeutic radiation, the radiotherapy device control apparatus 12 calculates a position of the irradiation target in real time based on the respiration signal acquired by the infrared camera 391 imaging the infrared marker M11, and controls the swing mechanism 321 such that the therapeutic radiation is irradiated toward the irradiation target.

In addition, the radiotherapy device control apparatus 12 has a correlation model indicating a relationship between the respiration signal and the position of the irradiation target. During production of the correlation model, the infrared camera 391 images the infrared marker M11, and the position information of a target site is acquired by the combination of the imaging radiation source 341 and the sensor array 361 and the combination of the imaging radiation source 342 and the sensor array 362. With this process, the relationship between the respiration signal and the position of the irradiation target is indicated, and the production of the correlation model becomes possible.

Figure 4:
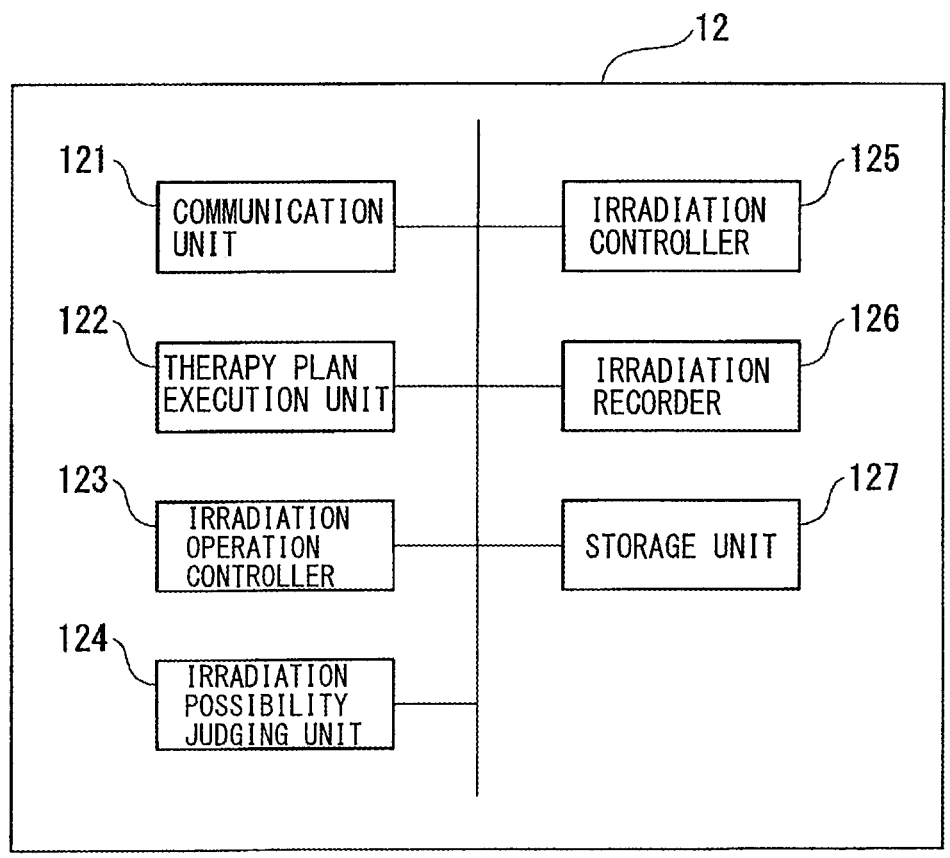
FIG. 4 is a schematic block diagram showing a functional structure of a radiotherapy device control apparatus according to the first embodiment of the present disclosure.

FIG. 4 is a schematic block diagram showing a functional structure of the radiotherapy device control apparatus 12. In FIG. 4, the radiotherapy device control apparatus 12 comprises a communication unit 121, a therapy plan execution unit 122, an irradiation operation controller 123, an irradiation possibility judging unit 124, an irradiation controller 125, an irradiation recorder 126, and a storage unit 127.

The communication unit 121 communicates with the therapy plan device 11 and the radiotherapy device 13. In particular, the communication unit 121 acquires information of the therapy plan defining an irradiation method of therapeutic radiation from the therapy plan device 11. In addition, the communication unit 121 acquires, from the radiotherapy device 13, the respiration signal obtained by the infrared camera 391 imaging the infrared marker M11, and the see-through images of the irradiation target imaged by the combination of the imaging radiation source 341 and the sensor array 361, and the combination of the imaging radiation source 342 and the sensor array 362.

The therapy plan execution unit 122 produces instruction information of a sequence of irradiations by the radiotherapy device, based on a therapy plan which is defined in advance, and instructs the irradiation operation controller 123 to execute a sequence of irradiations based on the instruction information.

The irradiation operation controller 123 controls operations of a device related to irradiation based on an irradiation condition included in the instruction information acquired from the therapy plan execution unit 122. The device includes, for example, the travel gantry 313, the O-ring 312, the swing mechanism 321, the multi leaf collimator 332, and the like. For example, the irradiation condition includes an irradiation angle of the therapeutic radiation, and the irradiation operation controller 123 calculates rotational angles of the travel gantry 313 and the O-ring 312. The irradiation operation controller 123 rotates the travel gantry 313 about the rotational axis A12, according to the calculated rotational angle of the travel gantry 313. Further, the irradiation operation controller 123 rotates the O-ring 312 about the rotational axis A11 according to the calculated rotational angle of the O-ring 312. Moreover, the irradiation operation controller 123 calculates an irradiation target position based on the position information of the infrared marker detected by the infrared camera 391 and acquired at a predetermined time interval, and the correlation mode, and controls the rotational angles of the swing mechanism 321 around the pan axis A21 and the tilt axis A22, so that the irradiation direction of the therapeutic radiation continuously tracks the irradiation target position. In addition, the irradiation operation controller 123 calculates a shape of an irradiation target (affecter part) based on the see-through images imaged by the imaging radiation source 341 and the imaging radiation source 342, and, according to the shape, operates the multi leaf collimator 332 so that the shape of the irradiation field matches the calculated shape. Moreover, the irradiation operation controller 123 controls whether or not to execute irradiation of the therapeutic radiation from the radiation irradiation device 331, via the irradiation controller 125.

The irradiation possibility judging unit 124 judges the possibility of irradiation based on a detection result of the irradiation target detector which detects a motion of the irradiation target. Specifically, the irradiation possibility judging unit 124 acquires an irradiation target position in consideration of the motion by respiration based on the correlation model calculated by the irradiation operation controller 123. Further, the irradiation possibility judging unit 124 calculates an actual three-dimensional position of the irradiation target (affected part) based on the see-through images imaged by the sensor arrays 361 and 362. The irradiation possibility judging unit 124 then calculates a difference between the acquired irradiation objective position and the position of the irradiation target calculated based on the see-through image, judges that irradiation is possible when the difference is within a predetermined range (for example, a few millimeters), and judges that the irradiation is not possible when the difference is outside the predetermined range.

The infrared camera 391, and the sensor arrays 361 and 362 are an example of the irradiation target detector described above.

The irradiation controller 125 controls as to whether or not the therapeutic radiation is to be irradiated based on the judgment result of the irradiation possibility judging unit 124. More specifically, when the irradiation of the therapeutic radiation is to be executed, for example, the irradiation controller 125 applies a voltage to an electron gun (not shown) of the radiation irradiation device 331 to generate an electron beam, and, when the irradiation is not to be executed, the irradiation controller 125 does not apply the voltage, and stops generation of the electron beam.

The irradiation recorder 126 records a history of interruption of the irradiation of the therapeutic radiation based on the judgment result of the irradiation possibility judging unit 124. Specifically, the irradiation recorder 126 records in the storage unit 127 states of the device at a start and an end of a period in which the irradiation of the therapeutic radiation is interrupted.

The storage unit 127 is formed using a storage device of the radiotherapy device control apparatus 12, and records various information.

The therapy plan execution unit 122, the irradiation operation controller 123, the irradiation possibility judging unit 124, the irradiation controller 125, and the irradiation recorder 126 may be realized, for example, by a CPU (Central Processing Unit) of the radiotherapy device control apparatus 12 reading and executing a program from the storage unit 127.

Figure 5:
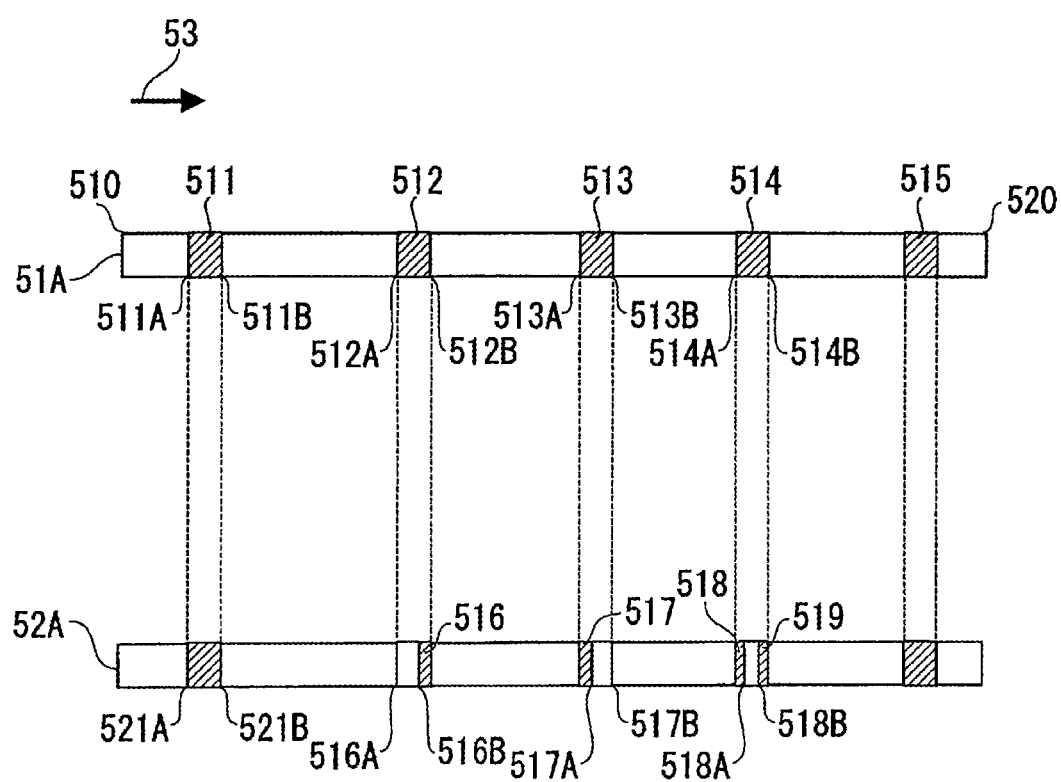
FIG. 5 is a diagram for explaining an irradiation method according to the first embodiment of the present disclosure.

FIG. 5 is a diagram for explaining an irradiation method of a first embodiment according to the present disclosure.

In FIG. 5, an irradiation method of the present embodiment will be described exemplifying a rotation operation of the travel gantry 313.

Reference numeral 51A represents an operation range of the travel gantry 313 and an irradiation result in a first sequence of irradiations. Reference numeral 510 represents an operation start position (for example, a rotational angle of 0 degree) of the travel gantry 313. Reference numeral 520 represents an operation end position (for example, a rotational angle of 360 degrees) of the travel gantry 313. An arrow of reference numeral 53 shows a rotational direction of the travel gantry 313 during the sequence of irradiations. In the sequence of irradiations in this example, a plan is employed in which the therapeutic radiation is continuously irradiated while the travel gantry 313 rotates in the range from reference numeral 510 to reference numeral 520. That is, while the travel gantry 313 rotates in the range from reference numeral 510 to reference numeral 520, the radiation irradiation device 331 continues to irradiate the therapeutic radiation toward the affected part. Portions assigned with reference numerals 511-515 represent a period in which the irradiation is interrupted because the tracking difference is large, during the first sequence of irradiations based on the instruction information. Other portions represent a period in which the radiation is irradiated in the first irradiation.

As shown in FIG. 5, in the present embodiment, even when the irradiation is interrupted due to the magnitude of the tracking difference during irradiation of the therapeutic radiation while rotating the travel gantry 313 based on the instruction information, the sequence of irradiations based on the instruction information is continued. In other words, no operation such as operations to stop the travel gantry 313 with the interruption of irradiation, and to slightly return the travel gantry 313 to match the interruption point is executed, and the travel gantry 313 continues to be rotated as planned. Further, in addition to the continued rotation of the travel gantry 313, if the tracking difference returns to a value in the allowable range during this period, the irradiation is again started. When the sequence of the irradiations is completed, the travel gantry 313 is rotated similar to the first irradiation, to execute a second sequence of irradiations targeted only to the irradiation interruption period represented by reference numerals 511-515 in which the irradiation is not executed.

Reference numeral 52A represents an irradiation result by the second sequence of irradiations. Reference numerals 516-519 each show a period in which irradiation is interrupted because the tracking difference is large even in the second sequence of irradiations. Because there remains a period in which the irradiation is not executed even in the second sequence of irradiations, the radiotherapy device 13 then executes a third sequence of irradiations by the control of the radiotherapy device control apparatus 12. In the third sequence, while the travel gantry 313 is rotated in a similar manner to the first and second sequences, the irradiation is executed only for the irradiation interruption period shown by reference numerals 516-519 for which irradiation is not executed. In this manner, the rotating operation of the travel gantry 313 and the irradiation targeted only to the irradiation interruption period are repeated until there no longer remains an irradiation interruption period. Here, as the operation of the device, an operation using the travel gantry 313 is explained, but the process is similar for a case, for example, in which the therapeutic radiation is irradiated while the travel gantry 313 and the O-ring 312 are moved simultaneously.

Figure 6:
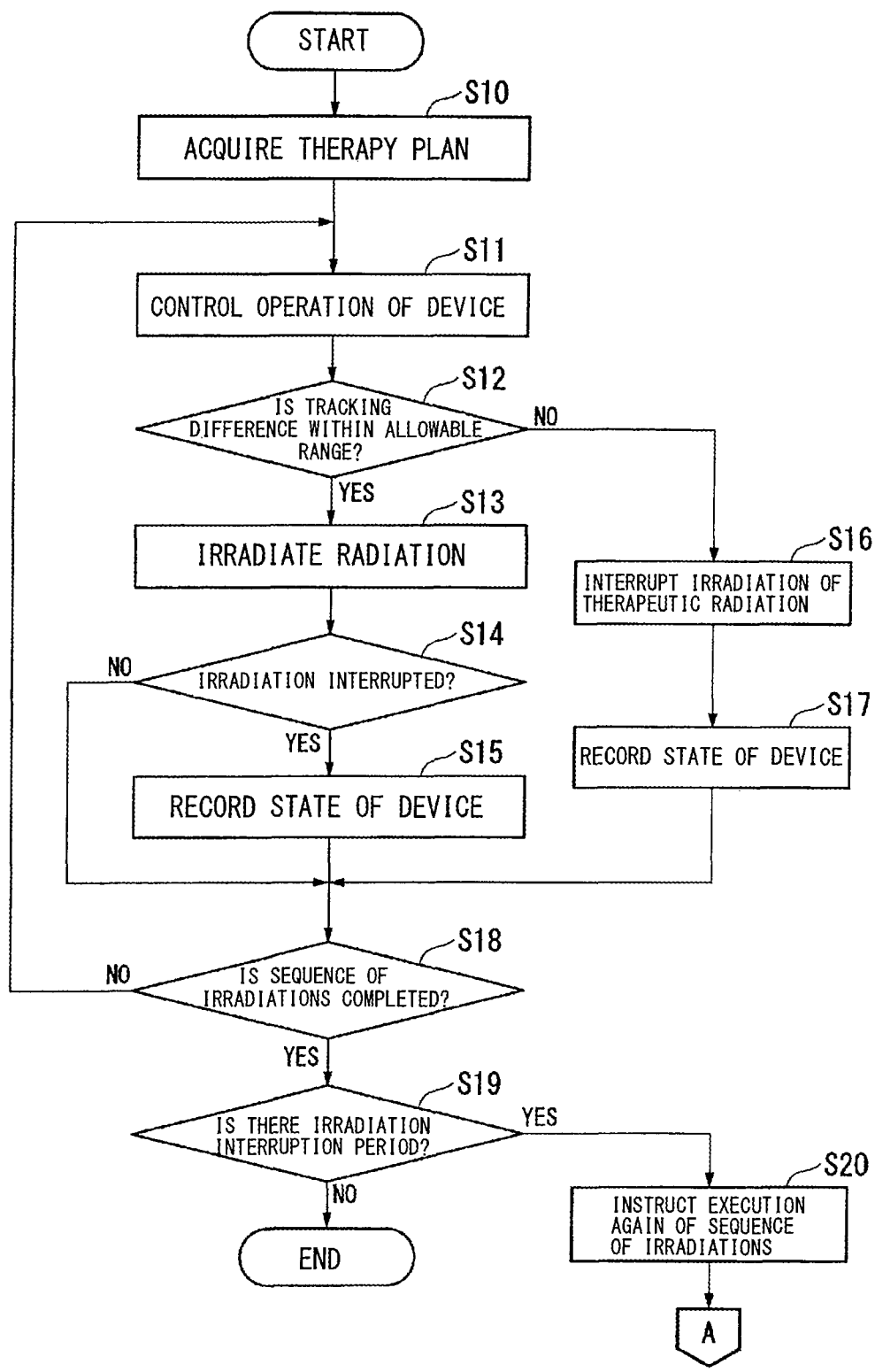
FIG. 6 is a first diagram showing a flowchart of irradiation control according to the first embodiment of the present disclosure.

FIG. 6 is a first diagram showing a flowchart of irradiation control according to the first embodiment of the present disclosure.

As an example, a case will be described in which the therapeutic radiation is continuously irradiated to the patient T11 while rotating the travel gantry 313 and the O-ring 312.

First, the communication unit 121 acquires the therapy plan from the therapy plan device 11 (step S10). The therapy plan includes information indicating the irradiation conditions such as the irradiation angle of radiation and necessary dosage for the sequence of irradiations. A sequence of irradiations refers to a collection of unit operations of, for example, continuously operating the travel gantry 313, the O-ring 312, or the like, and executing irradiation. The sequence of irradiations may correspond to all steps of therapy planned in the therapy plan or may correspond to, when the steps are separated into several smaller steps, the smaller steps. The communication unit 121 outputs the therapy plan to the therapy plan execution unit 122. Next, the therapy plan execution unit 122 produces instruction information of the sequence of irradiations based on the therapy plan, outputs the instruction information to the irradiation operation controller 123, and instructs the irradiation operation controller 123 to execute the sequence of irradiations.

Then, the irradiation operation controller 123 controls the operations of the device related to irradiation based on the irradiation condition included in the instruction information of the sequence of irradiations (step S11). For example, the irradiation operation controller 123 calculates the rotational angles of the travel gantry 313 and the O-ring 312 from the irradiation angle included in the irradiation condition, and rotates the travel gantry 313 and the O-ring 312 at predetermined velocities so that the irradiation unit 330 is located at a position where the radiation can be irradiated from an appropriate irradiation angle. The irradiation operation controller 123 calculates a shape of the irradiation target based on the see-through images imaged by the imaging radiation source 341 and the sensor array 361, and by the imaging radiation source 342 and the sensor array 362, and operates the multi leaf collimator, to match the shape of the irradiation field to the irradiation target. Further, the irradiation operation controller 123 calculates an irradiation objective position based on the position information of the infrared marker detected by the infrared camera 391, and the correlation model, adjusts the rotational angles around the pan axis and the tilt axis, and controls the orientation of the swing mechanism 321.

Next, the irradiation possibility judging unit 124 acquires the irradiation objective position from the irradiation operation controller 123, and calculates a difference between the irradiation objective position and a three-dimensional position of the irradiation target acquired from the see-through images of two directions. In addition, the irradiation possibility judging unit 124 reads a threshold of the tracking difference from the storage unit 127, compares the calculated difference and the read threshold of the tracking difference, and judges whether or not the difference is within an allowable range (step S12). The irradiation possibility judging unit 124 judges that the difference is within the allowable range when the calculated difference is less than or equal to the read threshold of the tracking difference, and judges that the difference is not within the allowable range when the calculated difference is larger than the read threshold of the tracking difference. The process is similar when it is possible to judge that the difference is within the allowable range by see-through image information of one direction.

When the irradiation possibility judging unit 124 judges that the tracking difference is within the allowable range (Yes in step S12), the irradiation operation controller 123 instructs the irradiation controller 125 to execute irradiation. The irradiation controller 125 causes the therapeutic radiation to be irradiated from the radiation irradiation device 331 (step S13).

The irradiation operation controller 123 also judges whether or not the irradiation of the therapeutic radiation is interrupted by the judgment of step S12 executed the previous time (step S14), and, when the irradiation of radiation is interrupted in the previous sequence, outputs to the irradiation recorder 126 information of the previous sequence such as the rotational angles of the travel gantry 313 and the O-ring 312, the positions of the leaves of the multi leaf collimator 332, the irradiation dosage, or the like, and instructs recording of the states of the device at the irradiation interruption end position. The irradiation recorder 126 records in the storage unit 127 the acquired states of the device (such as the rotational angles of the travel gantry 313 and the O-ring 312, the positions of the leaves of the multi leaf collimator 332, the irradiation dosage, or the like) at the irradiation interruption end position (step S15). When there is no interruption of irradiation, the process proceeds to step S18.

If the irradiation possibility judging unit 124 judges that the tracking difference is not within the allowable range (No in step S12), the irradiation operation controller 123 instructs interruption of irradiation to the irradiation controller 125 (step S16). The irradiation controller 125 stops irradiation of the therapeutic radiation from the radiation irradiation device 331. In the present embodiment, however, the operations of the device such as the travel gantry 313 are not stopped, and the operations based on the instruction information are continued. Then, the irradiation operation controller 123 outputs information at the irradiation interruption start position such as the rotational angles of the travel gantry 313 and the O-ring 312, the positions of the leaves of the multi leaf collimator 332, and the irradiation dosage, to the irradiation recorder 126, and instructs recording of the states of the device at the irradiation interruption position. The irradiation recorder 126 records in the storage unit 127 the acquired states of the device at the irradiation interruption start position (step S17). A range defined by the rotational angles of the travel gantry 313 or the like at the irradiation interruption start position and the irradiation interruption end position will be referred to as an irradiation interruption period.

Next, the irradiation operation controller 123 judges whether or not the sequence of irradiations instructed from the therapy plan execution unit 122 is completed regardless of whether or not the irradiation of the radiation is interrupted during the process (step S18), and, if the sequence is not completed, the processes from step S11 are repeated. If the sequence is completed, the irradiation operation controller 123 notifies the completion of the sequence of irradiations to the therapy plan execution unit 122.

Then, the therapy plan execution unit 122 reads the interruption history recorded by the irradiation recorder 126, and judges whether or not there exists an irradiation interruption period (step S19). If information of the irradiation interruption period is not recorded (No in step S19), the therapy plan execution unit 122 judges that all planned irradiations have been executed, and completes the irradiation process of the therapeutic radiation based on the therapy plan. When the steps are separated into smaller steps, processes similar to the processes from step S11 are executed for all of the smaller steps.

When information of the irradiation interruption period is recorded (Yes in step S19), the therapy plan execution unit 122 judges that the planned irradiations have not been completed, and instructs the irradiation operation controller 123 to again execute a sequence of irradiations based on the therapy plan (step S20).

In this manner, the radiotherapy device 13 executes the sequence of irradiations to the last irradiation without returning the states of the device regardless of presence or absence of interruption of irradiation by the tracking difference, and executes the irradiation of the planned therapeutic radiation to the extent possible.

Figure 7:
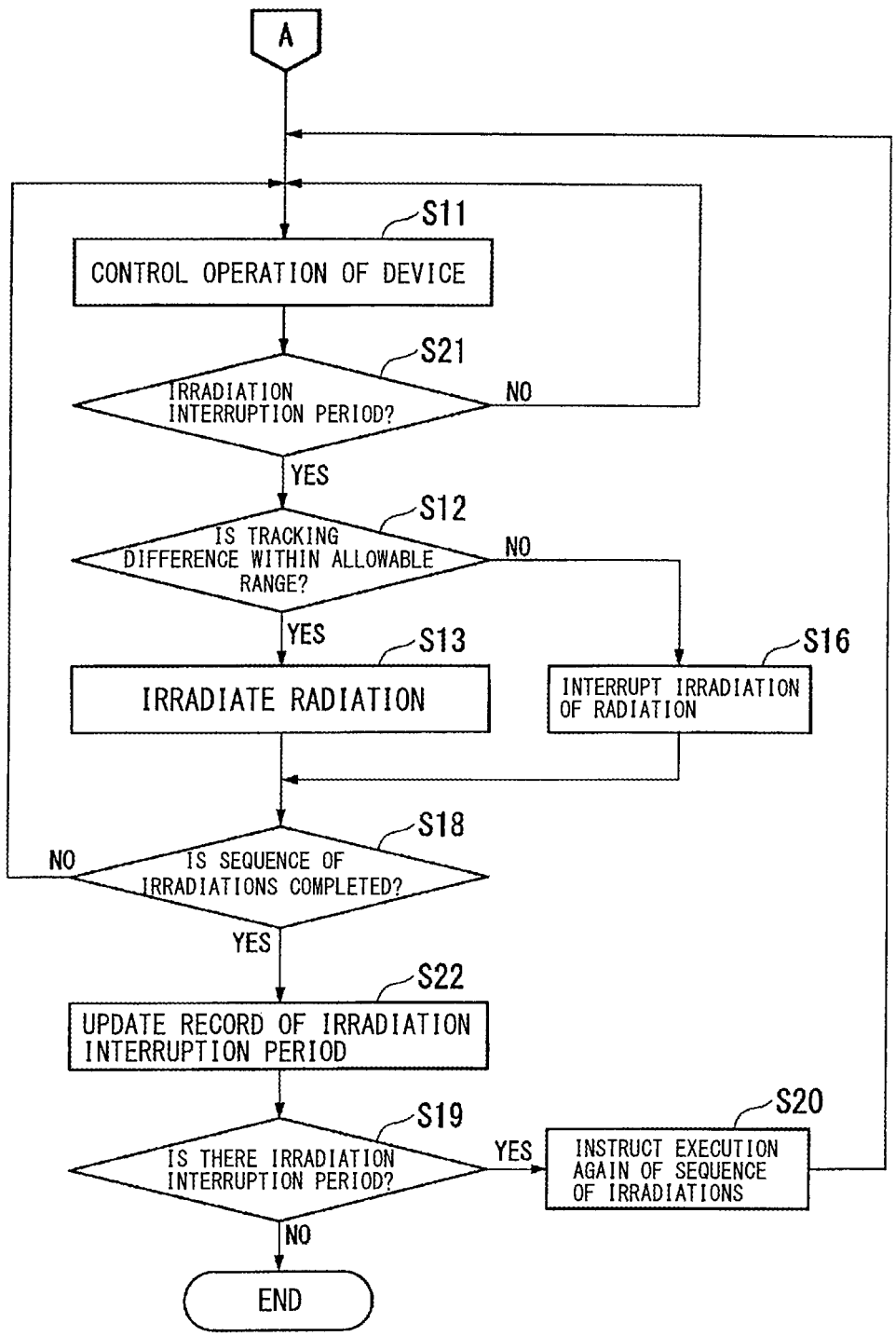
FIG. 7 is a second diagram showing a flowchart of irradiation control according to the first embodiment of the present disclosure.

FIG. 7 is a second diagram showing a flowchart of the irradiation control according to the first embodiment of the present disclosure.

With reference to FIG. 7, control executed on second and later sequences of irradiations when there exists an irradiation interruption period will be described. Processes identical to those in the process flow of FIG. 6 will be assigned the same reference numerals for description.

First, the irradiation operation controller 123 controls the operations of the device related to irradiation based on the irradiation condition included in the instruction information (step S11). Then, the irradiation operation controller 123 compares current rotational angles of the travel gantry 313 and the O-ring 312 and the rotational angles of the travel gantry 313 and the O-ring 312 of the irradiation interruption period recorded in the storage unit 127, and judges whether or not the current irradiation position is included in the irradiation interruption period (step S21). If the current irradiation position is not included in the irradiation interruption period (No in step S21), the irradiation is already completed, and the processes from step S11 are repeated. That is, the operations of the device are continued based on the instruction information.

If the current irradiation position is included in the irradiation interruption period (Yes in step S21), the irradiation operation controller 123 executes the irradiation of the therapeutic radiation based on the judgment of the irradiation possibility judging unit 124. First, the irradiation possibility judging unit 124 calculates a difference between the objective irradiation position and the irradiation target position calculated from the see-through image, and judges whether or not the tracking difference is within a predetermined range (step S12). If the tracking difference is within the predetermined range, the irradiation operation controller 123 instructs the irradiation of the radiation to the irradiation controller 125, and the irradiation controller 125 causes the radiation irradiation device 331 to irradiate the therapeutic radiation (step S13). If the tracking difference is not within the predetermined range, the irradiation operation controller 123 instructs interruption of the irradiation to the irradiation controller 125, and the irradiation controller 125 stops the irradiation of the therapeutic radiation from the radiation irradiation device 331 (step S16).

The irradiation operation controller 123 records in the storage unit 127 the information at the start and stopping of irradiation such as the rotational angles of the travel gantry 313 and the O-ring 312, the positions of the leaves of the multi leaf collimator 332, and the irradiation dosage, in correlation with information, for example, of the current number of sequences of irradiations being executed, every time the irradiation is executed.

Next, the irradiation operation controller 123 judges whether or not the operations of the device at the sequence of irradiations defined in the instruction information are completed (step S18), and if the operations are not completed, the processes from step S11 are repeated. If the operations are completed, the irradiation operation controller 123 instructs the irradiation recorder 126 to update the record of the irradiation interruption period. The irradiation recorder 126 updates the information of the irradiation interruption period recorded in the storage unit 127 (step S22). For example, when the irradiation interruption start position (for example, 511A on FIG. 5) of a certain irradiation interruption period recorded in a previous sequence of irradiations and information recorded by the irradiation operation controller 123 at the start of the irradiation of the current sequence of irradiations (for example, 521A of FIG. 5) are identical, and the information of the previous irradiation interruption end position (for example, 511B of FIG. 5) and the information of stopping of irradiation recorded by the irradiation operation controller 123 at the current time (for example, 521B of FIG. 5) are identical, the irradiation recorder 126 deletes, from the storage unit 127, the information of the irradiation interruption start position and the irradiation interruption end position of the irradiation interruption period previously recorded, as the irradiation based on the instruction information at the irradiation interruption period for which the irradiation is not executed previously is completed.

In addition, for example, when the information of the irradiation interruption start position of the previous time (for example, 512A of FIG. 5) and the information of the start of irradiation at the current time (for example, 516A of FIG. 5) are identical, and the information of the irradiation interruption end position of the previous time (for example, 512B of FIG. 5) and the information of the stopping of irradiation of the current time (for example, 516B of FIG. 5) differ from each other, the irradiation recorder 126 updates the information of the irradiation interruption start position of the previous time with the information of stopping of the irradiation of the current time. Further, when the information of the irradiation interruption start position of the previous time (for example, 513A of FIG. 5) and the information of the start of the irradiation of current time (for example, 517A of FIG. 5) differ from each other, and the information of the irradiation interruption end position of the previous time (for example, 513B of FIG. 5) and the information of the stopping of the irradiation of the current time (for example, 517B of FIG. 5) are identical, the irradiation recorder 126 updates the information of the irradiation interruption end position of the previous time with the information of the start of irradiation of the current time.

Further, for example, when the irradiation period of the current time is included in a certain irradiation interruption period of the previous time based on the rotational angles of the travel gantry 313 and the O-ring 312 at start and stop of the irradiation of the current time, the irradiation recorder 126 records information of the start of the irradiation of the current time (for example, 518A of FIG. 5) as the information of a new irradiation interruption end position corresponding to the irradiation interruption start position of the irradiation interruption period (for example, 514A of FIG. 5), and records the information of the stopping of the irradiation of the current time (for example, 518B of FIG. 5) as the information of a new irradiation interruption start position corresponding to the irradiation interruption end position of the irradiation interruption period (for example, 514B of FIG. 5). With this process, a range of the non-irradiation indicated by the information of the irradiation interruption period recorded in the storage unit 127 is gradually narrowed.

When the update process of the irradiation interruption period by the irradiation recorder 126 is completed, the irradiation operation controller 123 outputs completion of the sequence of mechanical operations to the therapy plan execution unit 122.

Then, the therapy plan execution unit 122 reads the record updated by the irradiation recorder 126, and judges whether or not there exists a record of an irradiation interruption period (step S19). If there is no record of information of the irradiation interruption period (No in step S19), the therapy plan execution unit 122 judges that all planned irradiations have been executed, and completes the irradiation process of the radiation based on the therapy plan.

If there is a record of information of the irradiation interruption period (Yes in step S19), the therapy plan execution unit 122 judges that the planned sequence of irradiations is not completed, and instructs the irradiation operation controller 123 to execute the sequence of irradiations based on the therapy plan (step S20). The irradiation operation controller 123 repeats the processes from step S11 in the process flow of FIG. 7. In this manner, the therapy plan execution unit 122 instructs the irradiation operation controller 123 to execute the sequence of irradiations, until there is no record of the irradiation interruption period.

In this manner, the radiotherapy device 13 repeats the sequences of irradiations until there is no non-irradiation period, and completes the therapy plan.

In the related art, when the tracking difference in the irradiation direction of the therapeutic radiation with respect to an affected part which may move frequently during tracking irradiation exceeds an allowable range, the devices must be recovered to the irradiation interruption point (in many cases, a state before the position is reached), which resulted in temporal and labor losses for the recovery. In particular, the recovery of the travel gantry 313 and the O-ring 312 required a long period of time. In addition, in the case of a patient in which the tracking difference outside of the allowable range occurs several times, in many cases, the patient is also a patient with a problem in respiration, and there has been a problem in that burden is placed on such a patient. In the present embodiment, even if there is an interruption of irradiation due to tracking difference during execution of the sequence of irradiations, the planned mechanical operations are executed to the last operation, and, when the tracking difference returns to a value within the allowable range, the irradiation is executed, so that the planned irradiation is executed as much as possible in the sequence of irradiations. In addition, the operations of the devices to return the states of the devices to the original states and matching to the interruption point are eliminated, and the therapy is completed by repeating the sequences of irradiations. Because of this, the repetition times of the mechanical operations having a large temporal loss may be reduced and the therapy time can be shortened.

The excess of the tracking difference over the allowable range can be considered to be about 0.1 seconds to 0.3 seconds in a typical respiration period (3 seconds to 4 seconds). In the method of the related art, if the irradiation is interrupted due to the tracking difference once every 3 seconds in VMAT irradiation which requires 30 seconds, there has been a possibility of 10 or more repetitions of the operations to irradiate shortly, to return the travel gantry 313 to the original position, to again match the states of the device to the interruption point, and to re-start irradiation. According to the present embodiment, the irradiation can be completed by repeating, 2-3 times, the operations of the device involved in the sequence of irradiations defined in advance. Thus, work efficiency is high, therapy time can be shortened, and the burden applied on the patient can be lessened.

Alternatively, when the sequence of irradiations is to be executed for a second or later time, the irradiation operation controller 123 may determine the rotational direction according to the position of the irradiation interruption period, and, for example, when the irradiation interruption period is concentrated in a range of at the last part of rotation of the first sequence of irradiations, control may be applied to rotate the travel gantry 313 in an opposite rotational direction.

In addition, in the above, a case is described in which the therapeutic radiation is continuously irradiated while operating the travel gantry 313, the O-ring 312, the multi leaf collimator 332, and the swing mechanism 321. However, the operations of the devices to which the present embodiment can be applied are not limited to these operations. For example, the present embodiment may be applied to a radiotherapy device which does not have the O-ring 312 and the swing mechanism 321, wherein the therapy is executed by operating the multi leaf collimator 332 while rotating the travel gantry 313. Alternatively, the present embodiment may be applied to a case, for example, where the travel gantry 313 and the O-ring 312 are fixed at positions of being rotated by predetermined rotational angles, and the irradiation is executed while operating at least one of the multi leaf collimator 332 and the wing mechanism 321.

<Second Embodiment>

A radiotherapy device control apparatus 12 according to a second embodiment of the present disclosure will now be described with reference to FIG. 8.

In the second embodiment, in addition to the control described above with reference to the first embodiment, the operation range of the device related to the irradiation is reduced so that the therapy time is further shortened. In particular, because the operations of the travel gantry 313 and the O-ring 312 require certain periods of time, the application of the present embodiment is effective.

Figure 8:
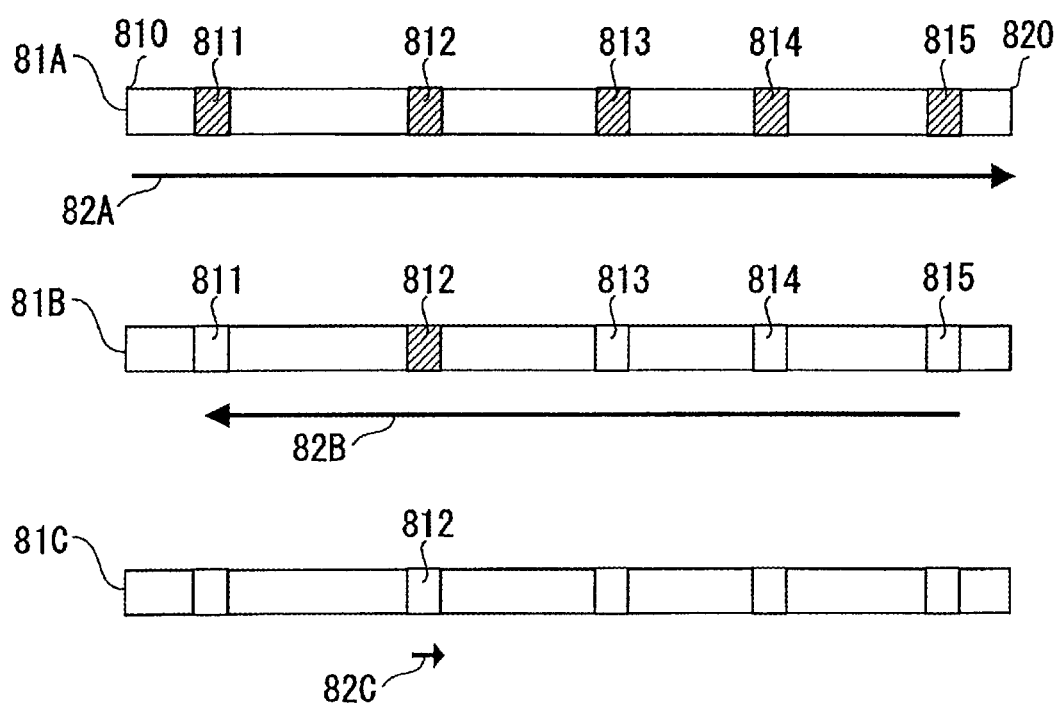
FIG. 8 is a diagram for explaining an irradiation method according to a second embodiment of the present disclosure.

FIG. 8 is a diagram for explaining an irradiation method according to the second embodiment of the present disclosure.

In FIG. 8, an irradiation method of the present embodiment will be described exemplifying a rotation operation of the travel gantry 313.

Reference numeral 81A represents an operation range and an irradiation result of the travel gantry 313 by a first sequence of irradiations. Reference numeral 810 represents an operation start position (for example, a rotational angle of 0 degree) of the travel gantry 313. Reference numeral 820 represents an operation end position (for example, a rotational angle of 360 degrees) of the travel gantry 313. Portions shown with reference numerals 811-815 show an irradiation interruption period due to a large tracking difference. Other portions show periods in which the radiation is irradiated by the first irradiation. An arrow of reference numeral 82A represents a rotational direction and an effective rotation range of the travel gantry 313 at the first sequence of irradiations. The travel gantry 313 executes a preliminary operation from a position slightly before the irradiation start position, in order to rotate at a predetermined velocity suited for therapy.

The effective rotation range is an operation range in which the rotation range by the preliminary operation is removed from the range of actual rotation of the travel gantry 313. The effective rotation range of the travel gantry 313 is shown by a length of the arrow 82A.

Reference numeral 81B shows an irradiation result by a second sequence of irradiations in the present embodiment. Similar to the first embodiment, reference numerals 811-815 show the periods in which the irradiation is to be executed in the second sequence of irradiations. The portion assigned with reference numeral 812 is a portion in which the irradiation is not executed due to the large tracking difference even in the second irradiation. Other portions shown with reference numerals 811 and 813-815 show that irradiation is executed in the second irradiation. An arrow of reference numeral 82B shows a rotational direction and an effective rotation range of the travel gantry 313 at the second sequence of irradiations. As shown by the arrow 82B, the effective rotation range of the travel gantry 313 at the second irradiation is smaller than that in the first irradiation. By limiting the operation range to a range necessary for irradiation, for example, the operation range of the travel gantry 313 can be narrowed compared to the first sequence of irradiations in which the travel gantry 313 is rotated one rotation from 0 to 360 degrees, and the time necessary for the irradiation can be shortened.

Similarly, reference numeral 81C shows an irradiation result by a third sequence of irradiations in the present embodiment. An arrow of reference numeral 82C shows a rotational direction and an effective rotation range of the travel gantry 313 at the third sequence of irradiations. Because the non-irradiated portion in the second sequence of irradiations is only the portion of reference numeral 812, the effective rotation range of the travel gantry 313 at the third irradiation is a very limited range. According to the present embodiment, for example, the travel gantry 313 can be moved directly from the position where the second sequence of irradiations is completed to the start position of the third sequence of irradiations, and thus, not only can the effective rotation range of the actual irradiation (third sequence of irradiations) be reduced, but also, the operation range including the preliminary operation can be reduced. A portion indicated with reference numeral 812 is irradiated at the third irradiation, and thus, the therapy plan execution unit 122 completes the irradiation process based on the therapy plan when the third sequence of irradiations is completed.

In the first embodiment, the effective rotation range of the travel gantry 313 is always a range shown by the arrow 82A. As is clear from FIG. 8, according to the present embodiment, the effective rotation range of the travel gantry 313 can be reduced according to the remaining non-irradiated period (irradiation interruption period), and thus, the therapy time can be further reduced.

In the above description, the rotation operation of the travel gantry 313 is exemplified, but the present embodiment can be similarly applied when the travel gantry 313 and the O-ring 312 are simultaneously operated, or, for example, when the travel gantry 313 is fixed at a certain angle and only the O-ring 312 is rotated. For example, reference numeral 81A of FIG. 8 may represent the operation range of a trajectory of the irradiation unit 330 by the rotation operation of the travel gantry 313 or the O-ring 312, and a configuration similar to the above may be applied.

A process flow of the present embodiment will now be described. In the present embodiment also, the first sequence of irradiations is similar to that of the first embodiment to step S19 of FIG. 6. In the present embodiment, in step S20, the therapy plan execution unit 122 identifies, based on the interruption history of the first sequence of irradiations by the irradiation recorder 126, a range which includes all of one or a plurality of irradiation interruption periods of the therapeutic radiation and in which the operations of the device are continuous for the first sequence of irradiations (for example, a range shown by the arrow 82B of FIG. 8). The therapy plan execution unit 122 produces new instruction information of a sequence of irradiations comprising irradiation conditions corresponding to the identified range based on the instruction information of the sequence of irradiations used in the first irradiation, and instructs the irradiation operation controller 123 to execute a sequence of irradiations based on the new instruction information which is produced. Similar processes are executed for second and later sequences of irradiations. In step S20 of FIG. 7, the therapy plan execution unit 122 produces new instruction information of a sequence of irradiations corresponding to a continuous range including all of the irradiation interruption periods, based on the instruction information of the sequence of irradiations used in the previous irradiation, and instructs the irradiation operation controller 123 to execute the new instruction information. The other processing steps are similar to those of the process flow of the first embodiment described with reference to FIG. 7.

According to the present embodiment, the therapy time can be further shortened.

Alternatively, a program for realizing all or a part of the functions of the radiotherapy device control apparatus 12 may be recorded on a computer-readable recording medium, and the program recorded on the recording medium may be read by a computer system and executed, to execute the processes of the various units. The "computer system" as described herein includes an OS and hardware such as peripheral devices.

The "computer system" as described herein also includes a webpage provision environment (or display environment) when the computer system uses the WWW system.

The "computer-readable recording medium" refers to a transportable medium such as a flexible disk, a magneto-optical disk, a ROM, a CD-ROM, or the like, and a storage device such as a hard disk drive or the like built in the computer system. The program described above may realize a part of the functions described above, and may be a program which realizes the above-described functions by a combination with a program already recorded on the computer system.

Further, the constituting elements in the above-described embodiments may be suitably replaced with known constituting elements within the scope and spirit of the present disclosure. In addition, the scope of the present disclosure is not limited to the above-described embodiments, and various modifications may be made within the scope and spirit of the present disclosure. The travel gantry 313 is one example of a gantry. The O-ring 312 is one example of a ring mechanism. The patient T11 is one example of a body to be irradiated.

INDUSTRIAL APPLICABILITY

According to the radiotherapy device control apparatus and the control method described above, the therapy time by the radiotherapy device can be shortened.

REFERENCE SIGNS LIST

1 RADIOTHERAPY SYSTEM; 11 THERAPY PLAN DEVICE; 12 RADIOTHERAPY DEVICE CONTROL APPARATUS; 13 RADIOTHERAPY DEVICE; 121 COMMUNICATION UNIT; 122 THERAPY PLAN EXECUTION UNIT; 123 IRRADIATION OPERATION CONTROLLER; 124 IRRADIATION POSSIBILITY JUDGING UNIT; 125 IRRADIATION CONTROLLER; 126 IRRADIATION RECORDER; 127 STORAGE UNIT; 311 TURN DRIVE DEVICE; 312 O-RING; 313 TRAVEL GANTRY; 321 SWING MECHANISM; 330 IRRADIATION UNIT; 331 RADIATION IRRADIATION DEVICE; 332 MULTI LEAF COLLIMATOR; 341, 342 IMAGING RADIATION SOURCE; 351, 361, 362 SENSOR ARRAY; 381 COUCH; 391 INFRARED CAMERA.

The invention claimed is:
1. A radiotherapy device control apparatus comprising:
a therapy plan execution unit that instructs execution of instruction information based on a therapy plan which is defined in advance;
an irradiation operation controller that controls an operation of a device provided on a radiotherapy device, based on an irradiation condition included in the instruction information;
an irradiation possibility judging unit that judges whether or not irradiation is possible based on a detection result of an irradiation target detector that detects a motion of an irradiation target;
an irradiation controller that controls execution and interruption of irradiation of a therapeutic radiation based on a result of the judgment; and
an irradiation recorder that records an interruption history of irradiation by the judgment of the irradiation possibility judging unit, wherein
the irradiation operation controller executes the operation of the device based on the instruction information to a last operation regardless of presence or absence of an interruption of the irradiation during execution of the instruction information.
2. The radiotherapy device control apparatus according to claim 1, wherein
the therapy plan execution unit repeatedly instructs, after the instruction information is executed and when an interruption history of irradiation is recorded by the irradiation recorder, execution of the instruction information until there is no record of the interruption history of irradiation, the irradiation operation controller controls the operation of the device based on the instruction, and the irradiation controller executes irradiation only for an irradiation interruption period recorded in the interruption history.

3. The radiotherapy device control apparatus according to claim 2, wherein the therapy plan execution unit produces, after the instruction information is executed and when one or a plurality of interruption histories of irradiation are recorded by the irradiation recorder, new instruction information targeted to a continuous range including all of a plurality of irradiation interruption periods recorded in the interruption history, and instructs the irradiation operation controller to execute the new instruction information.

4. The radiotherapy device control apparatus according to claim 1, wherein the irradiation possibility judging unit calculates a difference between a position of an irradiation target calculated based on a correlation model of a respiration signal and an irradiation position, which is defined in advance and a respiration signal which is generated in synchronization with respiration of a body to be irradiated detected by the irradiation target detector, and a position of the irradiation target acquired from an image of the body to be irradiated detected by the irradiation target detector, judges that irradiation is possible if the difference is within a predetermined range, and judges that irradiation is not possible if the difference is outside of the predetermined range.

5. The radiotherapy device control apparatus according to claim 1, wherein the device is a gantry which rotates an irradiation unit around an axis in a horizontal direction, and the irradiation operation controller controls a rotational angle of the gantry.

6. The radiotherapy device control apparatus according to claim 5, wherein the irradiation operation controller determines, after the instruction information is executed and when an interruption history of irradiation is recorded by the irradiation recorder, a rotational direction of the device based on a position of an irradiation interruption period recorded in the interruption history.

7. The radiotherapy device control apparatus according to claim 1, wherein the device is a ring which rotates an irradiation unit around an axis in a vertical direction, and the irradiation operation controller controls a rotational angle of the ring.

8. The radiotherapy device control apparatus according to claim 1, wherein the device is a ring which rotates an irradiation unit around an axis in a vertical direction and a gantry which rotates an irradiation unit around an axis in a horizontal direction, and the irradiation operation controller controls a rotational angle of the ring and a rotational angle of the gantry.

9. The radiotherapy device control apparatus according to claim 1, wherein the device is a multi leaf collimator, and the irradiation operation controller controls a position of each leaf of the multi leaf collimator.

10. The radiotherapy device control apparatus according to claim 1, wherein the device is a swing mechanism which supports an irradiation unit, and the irradiation operation controller controls a rotational angle of at least one of a pan axis and a tilt axis of the swing mechanism.

11. A control method of a radiotherapy device, comprising:

instructing execution of instruction information based on a therapy plan which is defined in advance;

controlling an operation of a device provided on the radiotherapy device, based on an irradiation condition included in the instruction information;

judging whether or not irradiation is possible based on a detection result of an irradiation target detector that detects a motion of an irradiation target;

controlling execution and interruption of irradiation of a therapeutic radiation based on a result of the judgment;

recording an interruption history of irradiation by the judgment; and executing the operation of the device based on the instruction information to a last operation regardless of presence or absence of an interruption of irradiation during execution of the instruction information.

* * * * *